US00PP15282P2

(12) United States Plant Patent
Randag

(10) Patent No.: US PP15,282 P2
(45) Date of Patent: Oct. 26, 2004

(54) CALLA LILY PLANT NAMED 'PICASSO'

(50) Latin Name: *Zantedeschia sprengeri*
Varietal Denomination: Picasso

(75) Inventor: Cecilius Jan-Jochem Randag, CJ 't Zand (NL)

(73) Assignee: Sande BV (NL)

( * ) Notice: Subject to any disclaimer, the term of this patent is extended or adjusted under 35 U.S.C. 154(b) by 0 days.

(21) Appl. No.: 10/684,878

(22) Filed: Oct. 14, 2003

(51) Int. Cl.[7] ..... A01H 5/00
(52) U.S. Cl. ..... Plt./263
(58) Field of Search ..... Plt./263

*Primary Examiner*—Kent Bell
*Assistant Examiner*—S. B. McCormick-Ewoldt
(74) *Attorney, Agent, or Firm*—Webb Ziesenheim Logsdon Orkin & Hanson, P.C.

(57) ABSTRACT

'Picasso' is a new variety of calla lily having a flower with a yellow-orange/purple colored spathe producing 1–15 flowers per tuber. The flower stems are about 50 cm in height. The leaves are green with many whitish spots and have a leathery texture.

3 Drawing Sheets

Botanical classification: *Zantedeschia sprengeri.*
Varietal denomination: 'Picasso'.

BACKGROUND OF THE NEW PLANT

The present invention comprises a new and distinct cultivar of calla lily, botanically known as *Zantedeschia sprengeri* and hereinafter referred to by the cultivar name 'Picasso'.

'Picasso' is a product of a planned breeding program which had the objective of creating *Zantedeschia* hybrids for cut flower production in a wide range of colors with a large, classic flower shape. The breeding program began in 1989 and the new cultivar is a seedling selected from the crossing of a *Zantedeschia sprengeri* seedling 92839 (female parent, unpatented) with a *Zantedeschia sprengeri* seedling 92864 (male parent, unpatented). 'Picasso' was originated in 1998 by the inventor C. J. J. (Cecilius Jan-Jochem) Randag in 't Zand, The Netherlands as one flowering plant within the progeny of the stated cross.

The first act of asexual reproduction of 'Picasso' by tissue culture was preformed by the inventor in August 2001 in 't Zand, The Netherlands. Subsequent asexual reproduction by tissue culture at the same location has demonstrated that the combination of characteristics as herein disclosed for the new cultivar are retained through successive generations of asexual reproduction.

The following traits have been repeatedly observed and determined to basic characteristics of Picasso which, in combination, distinguish this calla lily as a new and distinct cultivar:

1. White-Purple spathe;
2. Fast forcing time; and
3. High flower production.

Table 1 provides similarities and differences of 'Picasso' to its parents and the *Zantedeschia sprengeri* variety 'Cameo' (unpatented):

TABLE 1

| 'Picasso' | Similarities | Differences |
|---|---|---|
| '92839' (female parent) | Leaf shape | Spathe color and flower number |
| '92864' (male parent) | Leaf spots (maculation) | Flower shape, flower color, and leaf shape |
| 'Cameo' (unpatented) | Flower shape | Flower color |

BRIEF DESCRIPTION OF THE DRAWINGS

The accompanying photographic drawings illustrate the new variety, with the colors being as nearly true as is possible with color illustrations of this type.

DESCRIPTION OF THE NEW PLANT

Figure 1:
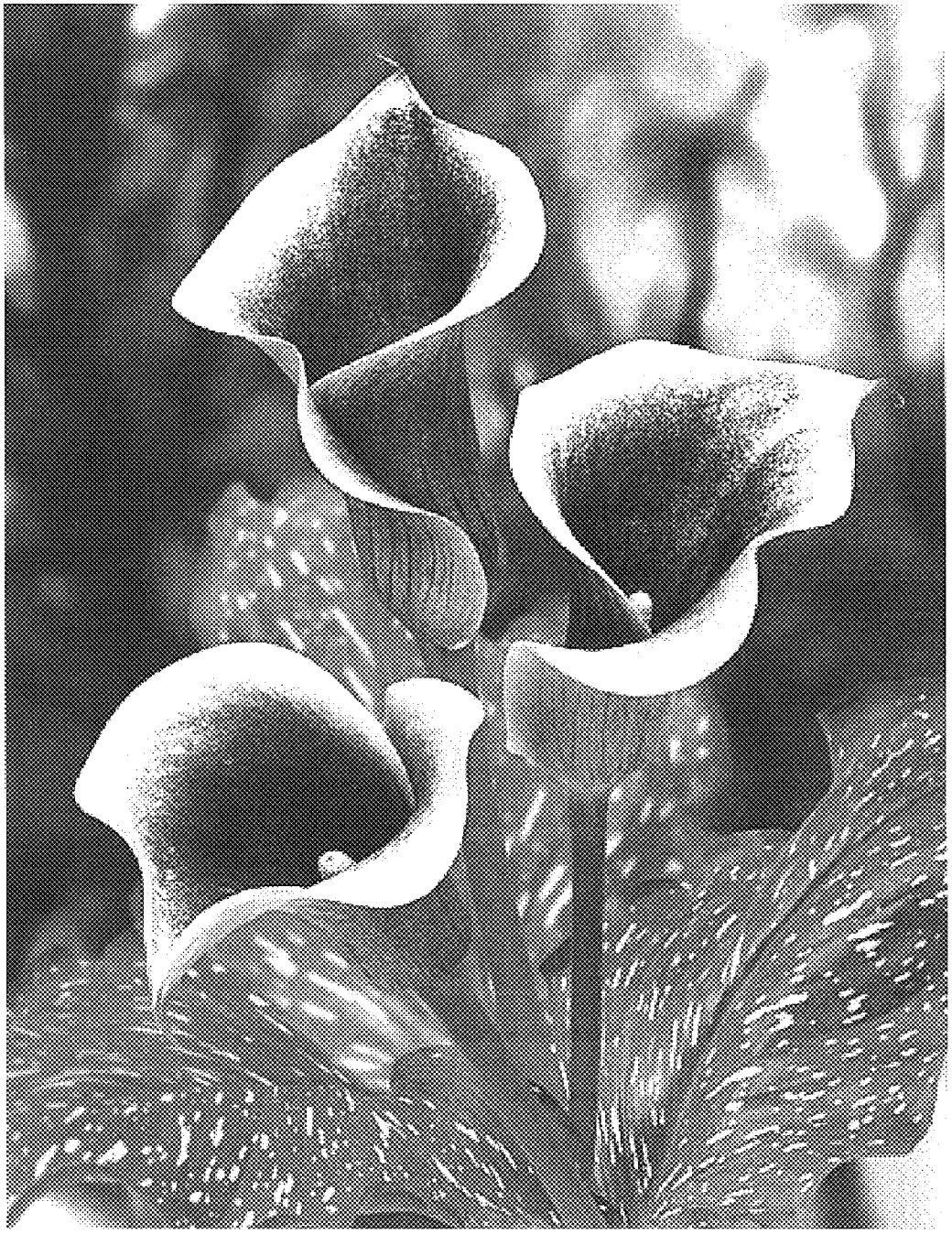
FIG. 1 is a close-up photograph of three 'Picasso' flowers.
Figure 2:
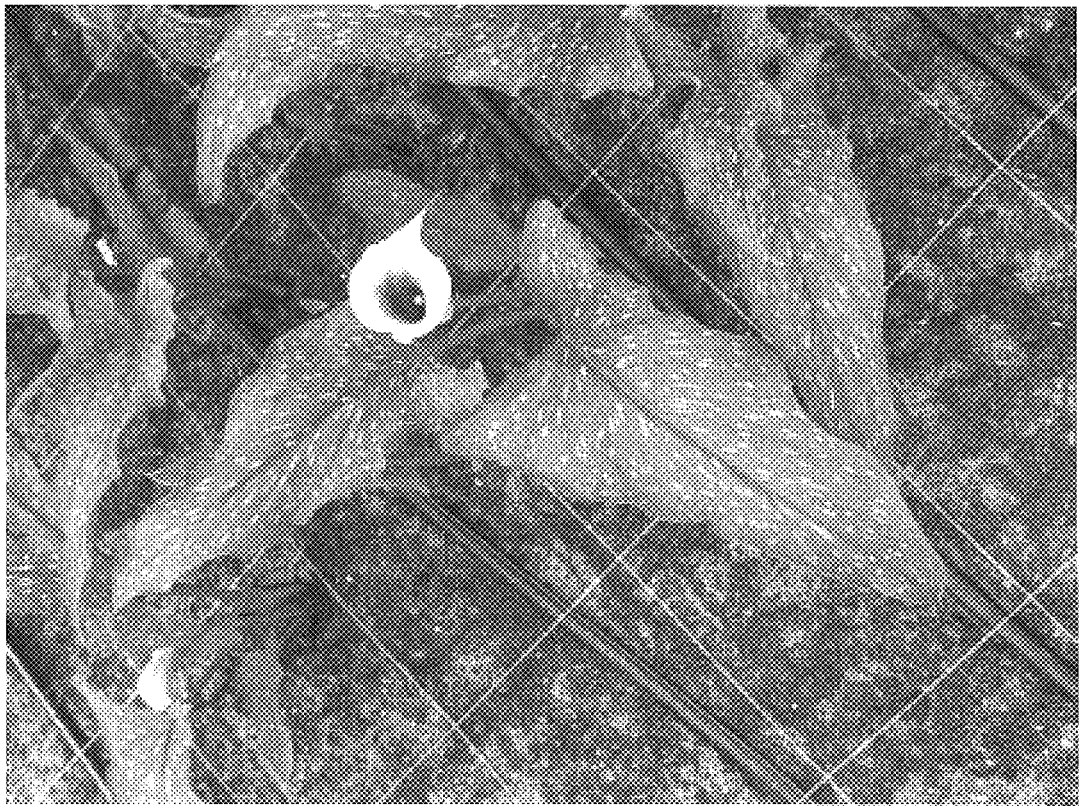
FIG. 2 is a photograph of a single flower of the new variety.
Figure 3:
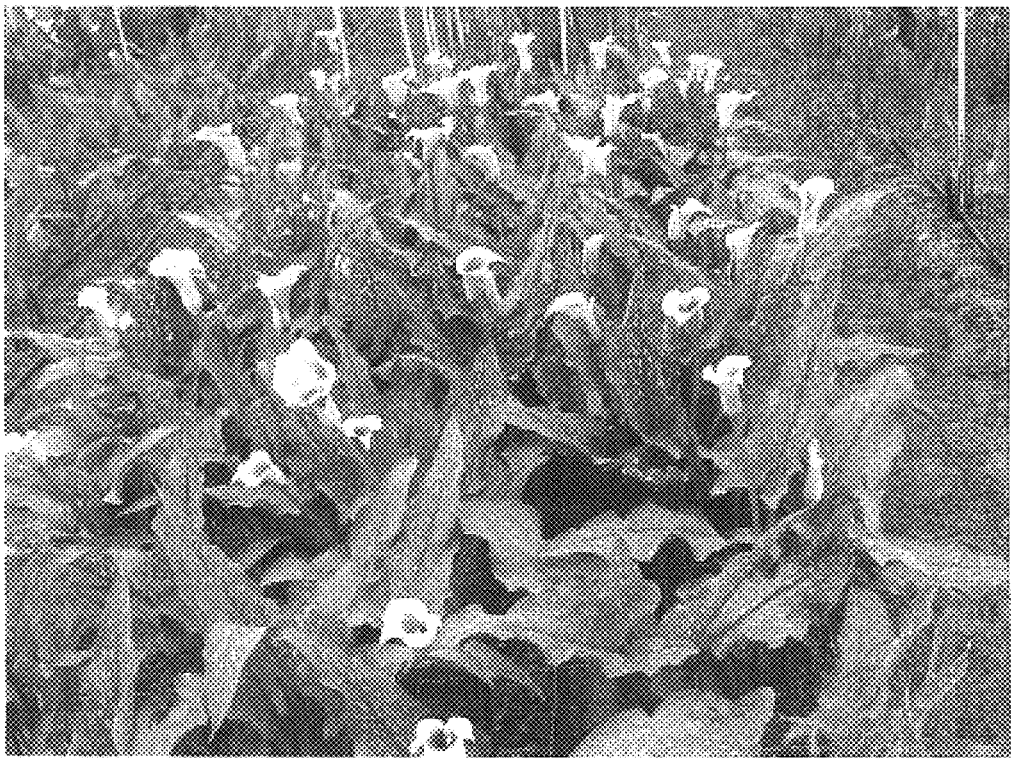
FIG. 3 is a field of 'Picasso' clones.

The following observations, measurements and comparisons describe plants grown in 't Zand, The Netherlands under greenhouse conditions which approximate those generally used in horticultural practice. Color references are made to the R.H.S. Colour Chart of The Royal Horticultural Society of London, except where general color terms of ordinary significance are used.

THE PLANT

Size:
*Height of the leaf canopy above the soil.*—50–65 cm.
*Height of top of flower above the soil.*60–70 cm.
*Diameter.*—30–45 cm.
*Form.*—Erect.

Number of flowers per tuber:
*Size 9–12 cm in diameter.*—1–2 flowers.
*Size 12–15 cm in diameter.*—3–4 flowers.
*Size 15–18 cm in diameter.*—5–10 flowers.

Branches:
*Character.*—Many, like the variety 'Celeste'.
*Average number.*—4.
*Color.*—Between Green group RHS 143A and Yellow-Green group RHS 144A, with spots of Red group RHS 53A.
*Length.*—40–50 cm.
*Diameter.*—10–15 cm.

Leaves:
*Size.*—Width: 10–15 cm. Length: 20–30 cm.
*Number per plant.*—7–25.
*Shape.*—Sagittate.
*Color.*—Upper surface: Green group RHS 137A–137B, with specks of RHS 4D. Lower surface: Green group RHS 137A–137B.
*Margin.*—Wavy.
*Veins.*—Configuration: Pinnate. Color: Yellow-Green group RHS 144A.
*Surface quality.*—Leathery.
*Petiole.*—Length: 30–50 cm. Color: Lower surface is between Yellow-Green group RHS 146B and RHS 146C with red spots of Red Group RHS 53A. Upper surface is between Yellow-Green group RHS 146B and RHS 146C.

Roots:
*Color.*—White.
*Branching.*—Not different from other *Zantedeschia.*

THE FLOWER

Spathe:
*Size.*—Length: 6–9 cm. Width: 5–7 cm.
*Color.*—Upper surface: Base colour is Green-Yellow group 1D with a second colour of purple between Purple group RHS 76A and Red-Purple group RHS 74B. Lower surface: Base colour is Green-Yellow group 1D with a second colour of purple between Purple group RHS 76A and Red-Purple group RHS 74B.
*Veins.*—Color: Varies between Purple group RHS 76A and Red-Purple group RHS 74B.
*Shape.*—Round.

Spadix:
*Size.*—Length: 20–50 mm. Diameter: 2–7 mm.
*Color.*—Yellow-Orange group between RHS 17A and RHS 17B.
*Position relative to spathe.*—Upright.

Peduncle:
*Size.*—Length: 50–65 cm. Diameter: 8–10 mm.
*Color.*—Varies between Yellow-Green group RHS 146B and RHS 146C.

Reproductive organs:
*Location of female organs.*—Basal position of the spadix.
*Location of male organs.*—Upper position of the spadix.
*Perianth.*—Conspicuous.
*Stamens.*—Not visible before pollen release.
*Pistil.*—Length: About 1 mm.

GENERAL

Disease resistance: No unusual susceptibility to disease.
Pest resistance: No unusual susceptibility to pests.
Heat tolerance: No heat tolerance.
Hardiness: Not hardy.
Flowering: Tubers planted in a greenhouse in The Netherlands in February produce flowers in April. Tubers planted outdoors in The Netherlands in May produce flowers in July.
Lastingness: About two weeks on the plant.
Fragrance: None.

I claim:

1. A new and distinct variety of calla lily plant named 'Picasso' as described and illustrated.

* * * * *